United States Patent
Baumgarten

(10) Patent No.: US 12,076,264 B2
(45) Date of Patent: Sep. 3, 2024

(54) ARM SLING APPARATUS

(71) Applicant: Keith M. Baumgarten, Sioux Falls, SD (US)

(72) Inventor: Keith M. Baumgarten, Sioux Falls, SD (US)

( * ) Notice: Subject to any disclaimer, the term of this patent is extended or adjusted under 35 U.S.C. 154(b) by 0 days.

(21) Appl. No.: 17/473,545

(22) Filed: Sep. 13, 2021

(65) Prior Publication Data

US 2022/0079801 A1 Mar. 17, 2022

Related U.S. Application Data

(63) Continuation-in-part of application No. 17/023,841, filed on Sep. 17, 2020, now abandoned.

(51) Int. Cl.
*A61F 5/37* (2006.01)

(52) U.S. Cl.
CPC .................. *A61F 5/3746* (2013.01)

(58) Field of Classification Search
CPC .......... A61F 5/01; A61F 5/0118; A61F 5/013; A61F 5/05858; A61F 5/3746; A61F 5/3738; A61F 5/37; A61F 5/3715; A61F 5/3723; A61F 5/373; A61F 5/3753; A61F 13/00; A41D 13/1245; A41D 1/04
USPC ........ 602/4, 60, 62; 128/846, 869, 873, 874, 128/878, 881
See application file for complete search history.

(56) References Cited

U.S. PATENT DOCUMENTS

| | | | |
|---|---|---|---|
| 941,277 A * | 11/1909 | Schmidt | A41F 9/02 2/102 |
| 3,515,131 A * | 6/1970 | Stevens | A61F 5/3738 602/20 |
| 5,086,762 A | 2/1992 | Chee | |
| 5,095,894 A * | 3/1992 | Marble | A61F 5/3746 602/62 |
| 6,406,449 B1 | 6/2002 | Moore | |
| 6,453,904 B1 * | 9/2002 | Wilson | A61F 5/3746 128/874 |
| 6,709,411 B1 | 3/2004 | Olinger | |
| 6,945,945 B2 | 9/2005 | Givler | |
| 8,273,041 B2 | 9/2012 | Goumas | |
| 8,454,544 B2 | 6/2013 | Barnes | |
| 9,668,902 B1 * | 6/2017 | Krenzel | A61F 5/3753 |

(Continued)

FOREIGN PATENT DOCUMENTS

CA 2259889 2/2005

OTHER PUBLICATIONS

U.S. Appl. No. 17/023,841, filed 2020).*
U.S. Appl. No. 17/023,841, filed 2022).*

*Primary Examiner* — Caitlin A Carreiro
(74) *Attorney, Agent, or Firm* — Jeffrey A. Proehl; Woods, Fuller, Shultz & Smith, PC

(57) ABSTRACT

Illustrative embodiments of a sling apparatus for supporting an arm of a person include a garment to be worn on the torso, and arm support elements mounted on the garment that are configured to support the arm of the person wearing the garment in at least two positions with respect to the torso. Illustrative implementations of the two positions include a first position of the arm having the elbow extended with a shoulder associated with the arm of the person being in a neutral rotation orientation, and a second position of the arm having the shoulder associated with the arm being in an adducted, internal rotation position with the elbow flexed.

20 Claims, 14 Drawing Sheets

(56) References Cited

U.S. PATENT DOCUMENTS

| | | | | |
|---|---|---|---|---|
| D794,252 S | * | 8/2017 | Grimmett | D29/101.4 |
| 10,517,752 B2 | | 12/2019 | Reinhardt | |
| 2010/0267525 A1 | | 10/2010 | Tanner | |
| 2011/0005525 A1 | * | 1/2011 | Barnes | A61F 5/3723 |
| | | | | 128/845 |
| 2012/0123307 A1 | | 5/2012 | Figurski | |
| 2015/0094635 A1 | | 4/2015 | Keller | |
| 2016/0256311 A1 | * | 9/2016 | Lemmon | A61F 5/3738 |
| 2018/0153723 A1 | | 6/2018 | Sotereanos | |
| 2018/0193180 A1 | | 7/2018 | Bejarano | |

* cited by examiner

ARM SLING APPARATUS

REFERENCE TO RELATED APPLICATIONS

This application is a continuation in part of U.S. non-provisional patent application Ser. No. 17/023,841, filed Sep. 17, 2020, the entirety of which is hereby incorporated by reference.

BACKGROUND

Field

The present disclosure relates to rehabilitation body supports and more particularly pertains to a new arm sling apparatus for providing versatility in the positions in which the arm can be supported by the apparatus.

SUMMARY

In one aspect, the present disclosure relates to a sling apparatus for supporting an arm of a person with respect to a torso of the person, with the arm having an upper arm portion and a lower arm portion. The sling apparatus may include a garment configured to be worn on the torso of the person, with the garment having a front for positioning adjacent to a front of the torso, a back for positioning adjacent to a back of the torso, and at least one lateral side extending between the front and back for positioning adjacent to a side of the torso. The garment may have at least one arm opening in the at least one lateral side for receiving the arm of the person. The sling apparatus may also include arm support elements mounted on the garment and configured to support the arm of the person wearing the garment in at least two positions with respect to the torso. The at least two positions may include a first position of the arm having the elbow extended with a shoulder associated with the arm of the person being in a neutral rotation orientation and a second position of the arm with the elbow flexed and the shoulder associated with the arm being in an adducted, internal rotation position.

There has thus been outlined, rather broadly, some of the more important elements of the disclosure in order that the detailed description thereof that follows may be better understood, and in order that the present contribution to the art may be better appreciated. There are additional elements of the disclosure that will be described hereinafter and which will form the subject matter of the claims appended hereto.

In this respect, before explaining at least one embodiment or implementation in greater detail, it is to be understood that the scope of the disclosure is not limited in its application to the details of construction and to the arrangements of the components set forth in the following description or illustrated in the drawings. The disclosure is capable of other embodiments and implementations and is thus capable of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present disclosure. It is important, therefore, that the claims be regarded as including such equivalent constructions insofar as they do not depart from the spirit and scope of the present disclosure.

The advantages of the various embodiments of the present disclosure, along with the various features of novelty that characterize the disclosure, are disclosed in the following descriptive matter and accompanying drawings.

BRIEF DESCRIPTION OF THE DRAWINGS

The disclosure will be better understood and when consideration is given to the drawings and the detailed description which follows. Such description makes reference to the annexed drawings wherein.

DETAILED DESCRIPTION

Figure 1:
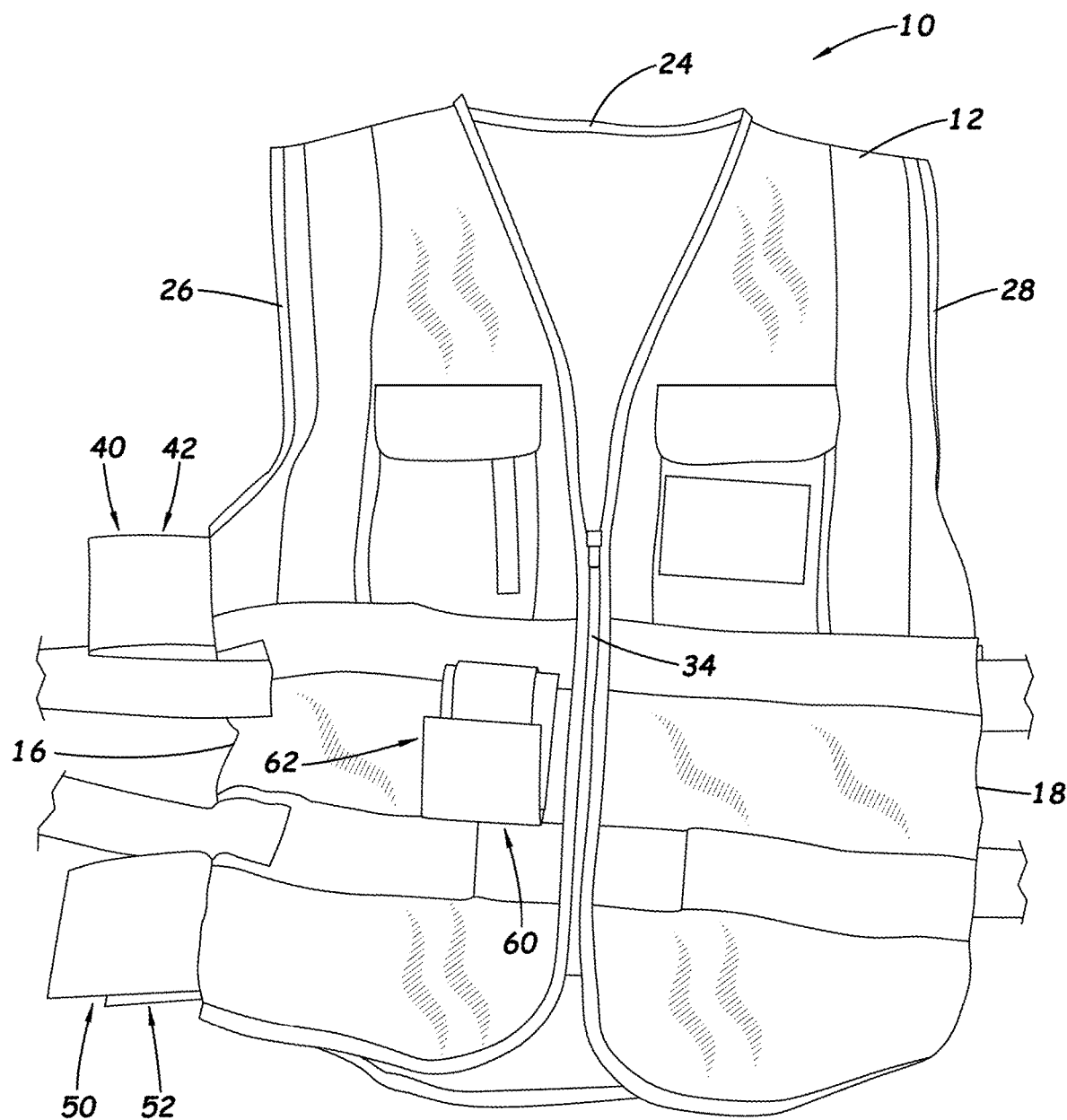
FIG. 1 is a schematic front view of an illustrative embodiment of a new sling apparatus according to the present disclosure.

With reference now to the drawings, and in particular to FIGS. 1 through 12 thereof, a new arm sling apparatus embodying the principles and concepts of the disclosed subject matter will be described.

Traditional rehabilitative arm supports, or arm slings, immobilize the elbow of the user of the sling in a flexed position, but the applicant has recognized that the usage of traditional arm slings can be problematic. For example, traditional arm slings promote prolonged elbow flexion which has been shown to increase the pressure within the cubital tunnel through which the ulnar nerve courses, and as a result putting the person at risk for developing symptoms of ulnar neuritis. Moreover, when used inappropriately, traditional arm slings may not support the wrist adequately, causing the sling user to maintain a hyper flexed position of the wrist that puts the patient at risk for developing symptoms of carpal tunnel syndrome.

The applicant has further recognized that distal peripheral neuropathy, which includes cubital tunnel syndrome and carpal tunnel syndrome, is a common complication after shoulder surgery and is likely due to contemporary methods of postoperative shoulder immobilization.

The applicant has developed a novel sling apparatus which maintains the user's arm in an elbow extended position that can be used to minimize the opportunity for the onset of symptoms of ulnar neuritis after shoulder surgery and can be used to treat symptoms of ulnar neuritis that arise de novo. The elbow extended position provided by the sling apparatus of the disclosure may be considered an optimal choice for use during sleep once the patient is comfortable sleeping in the supine position. In addition, when the sling is used by the patient in the supine position, the patient's wrist is immobilized against the torso and functionally maintains the wrist in the neutral position. As a result, the sling apparatus of the disclosure may also prevent the onset of carpal tunnel symptoms after shoulder surgery.

Further, the applicant has recognized that the majority of arm sling designs currently utilized will maintain the user's arm in complete internal rotation (for anti-rotation and internal rotation sling designs) to partial internal rotation (for abduction sling designs), and that very few of the currently utilized sling designs precisely maintain the arm in a neutral position. Although neutral rotation arm slings are designed to maintain the arm in neutral rotation, these designs often allow the immobilized arm to rotate into an internal rotated position. Moreover, there does not appear to be a consensus as to which type of sling (e.g., abduction sling vs. an internal rotation sling) is optimal for a patient after shoulder surgery, although some advantage has been suggested in using a neutral rotation sling over an internal rotation sling to provide improvements in range of motion and decreased night pain after anatomic total shoulder arthroplasty. The applicant has recognized that while further studies need to be performed regarding the optimal positioning after shoulder surgery, there appear to be benefits to immobilizing the arm in either a neutral rotation position or a position with mild external rotation.

The sling apparatus of the present disclosure provides the ability to immobilize the user's arm in the extended position with the shoulder being maintained in a neutral rotation position which has been shown to be beneficial in patients undergoing anatomic total shoulder arthroplasty and may have benefits after other shoulder surgeries such as arthroscopic rotator cuff repair.

Advantageously, the sling apparatus of the present disclosure is a dual positioning sling which provides the patient and the physician with a choice between more than one position to support the arm. As a result, the supportive position may be changed for different conditions or situations. For example, if the shoulder girdle of the user fatigues when the arm has been maintained in the elbow extension/shoulder neutral rotation position (e.g. due to the weight of the arm not being supported by the sling apparatus), the user can transition his or her arm to the internal rotation position which supports the weight of the arm more substantially than the elbow extension/shoulder neutral rotation position.

As a further example, immediately after surgery, when the patient has little motor control of his or her arm secondary to a peripheral nerve block, or when the patient is in a seated position, the internal rotated position may be more beneficial. Moreover, when the patient is seated, it may be very uncomfortable to have the elbow extended with the arm immobilized at the side.

The applicant has also recognized that immobilization of the arm after surgery using traditional arm slings can make it difficult to perform activities of daily living and light work activities (like computer work). However, arm slings able to provide support in a neutral rotation can permit better work performance and patient satisfaction as compared to slings which only provide support in an internal rotation position.

Advantageously, the sling apparatus of the present disclosure may be used as a functional sling when complete arm immobilization (e.g., in an extension position or in an internal rotation position) may not be desired. The sling apparatus permits the upper arm above the elbow to be immobilized in the adducted position and held against the torso, thereby protecting the shoulder, while allowing free motion at the elbow, wrist and hand of the arm and further allowing self-limited active internal and external rotation of the shoulder. In more protected and safe environments, the sling apparatus of the present disclosure permits patients to handle light objects, perform computer and sedentary work, feed themselves, and perform hygiene tasks, which are functions that are difficult to perform utilizing contemporary slings.

Further, the applicant recognizes that the application of low levels of controlled force may be beneficial to the healing of the rotator cuff, and that complete removal of the load from the rotator cuff may be detrimental to rotator cuff healing, possibly suggesting that it may be beneficial to not use any sling immobilization or to allow early active range of motion after rotator cuff repair surgery. The sling apparatus of the present disclosure may provide patients with more functional use of their postoperative extremity compared to traditional arm slings while still providing protection to the operative arm compared to not utilizing a sling at all.

Still further, the applicant has recognized that traditional arm slings often utilize a strap that traverses the neck and trapezius area of the user, which may contribute to neck and trapezial pain, and may even cause carotid hypersensitivity syndrome that can result in dizziness and syncope and spinal accessory nerve palsy. The sling apparatus of the present disclosure utilizes a garment which may engage a relatively large area of the user's torso and thus does not concentrate pressure on the user's neck, and consequently is less likely to cause neck pain or the rare complications that have been associated with a sling that utilizes a strap that courses around the neck. Moreover, while some patients have difficulty learning how to correctly don and maintain the appropriate arm position in traditional arm slings, as the wearing of a sling is not familiar or intuitive, the garment of the sling apparatus of the present disclosure may be similar to a vest which is familiar to the patient and is difficult to wear incorrectly.

In one aspect, the present disclosure relates to a sling apparatus 10 for supporting an arm 2 of a person 1, which may include an upper arm portion 3 and a lower arm portion 4 with an elbow in between the portions 3, 4. The sling apparatus 10 may support the arm in at least two positions of the arm with respect to the torso 5 of the person. In some embodiments, a first position of the arm 2 of the person may have the elbow of the arm extended with the shoulder of the person in a neutral rotation orientation (see FIG. 3A), which may have the lower arm portion of the person secured to the lateral aspect of the torso of the person, and a second position may have the arm of the person in an adducted, internal rotation position of the arm (see FIG. 3B), which may have the elbow of the person flexed with the lower arm portion secured to the ventral or anterior aspect of the torso of the person. In some implementations, a third position of the arm 2 has the upper arm portion 3 constrained in a position adjacent to the torso 5, but the lower arm portion 4 is unconstrained and generally free to move relative to the torso (see FIG. 3B).

The sling apparatus 10 may include a garment 12 which is configured to be worn by the person 1 using the apparatus 10 who may be a patient under medical supervision. The garment 12 may be configured to be worn on the torso 5 of the person such that the garment 12 covers, or substantially covers, the torso from the shoulders down to a point proximate to the waist of the person. In greater detail, the garment 12 includes a front 14 for positioning adjacent to the front of the person's torso, and a back 15 for positioning adjacent to the back of the person's torso. The lateral sides 16, 17 of the garment 12 may extend between the front 14 and back 15 for positioning adjacent to sides of the person's torso. The garment 12 has an inner extent or surface 20 for positioning against (or in close proximity to) the person's torso, and an outer surface 22 may be located opposite of the inner surface 24 on the garment for positioning away from the person's torso.

In further detail, the garment 12 may have a neck opening 24 which extends through the garment generally between the front 14 and back 15 for receiving the neck of the person wearing the garment duck opening 24. A pair of arm openings 26, 28 may extend through the garment 12 at the lateral sides 16, 17 between the front and back of the garment for receiving the respective arms of the person. A torso opening 30 may be located on the garment 12 opposite of the neck opening 24 to permit a portion of the person's torso 3 to extend out of the garment 12. Illustratively, the garment 12 may comprise a vest garment which generally lacks sleeves for receiving the arms of the person wearing the garment. The outer surface 22 of the front 14 of the garment may have a front region that extends between the neck opening 24 and the torso opening 30 defined by the lower edge 32. The outer surface 22 of the back 15 of the garment may have a back region that extends between the neck opening 24 and the torso opening 30. The outer surface 22 of the lateral sides 16, 18 of the garment may each have a side region that extends between a respective arm opening 26, 28 and the torso opening 30.

A slit 34 may be formed on the garment 12 to facilitate donning and doffing the garment on the torso of the person. The slit 34 may be positioned on, and extend across, the front 14 of the garment, and may extend from the neck opening 24 to the torso opening 30 to permit the garment to effectively be opened up to simplify placing the garment on the torso and removing the garment from the torso. Suitable closure means, such as a zipper closure, may be mounted along the edges of the material forming the slit to selectively join the edges forming the slit. Optionally, the slit 34 may be omitted in some embodiments of the garment 12.

The sling apparatus 10 may also include arm support elements 38 configured to support the arm 2 of the person 1 wearing the garment 12, and the support elements 38 may be configured to support the arm in at least two positions of the arm, such as a neutral rotation orientation position and an adducted, internal rotation position.

Figure 2:
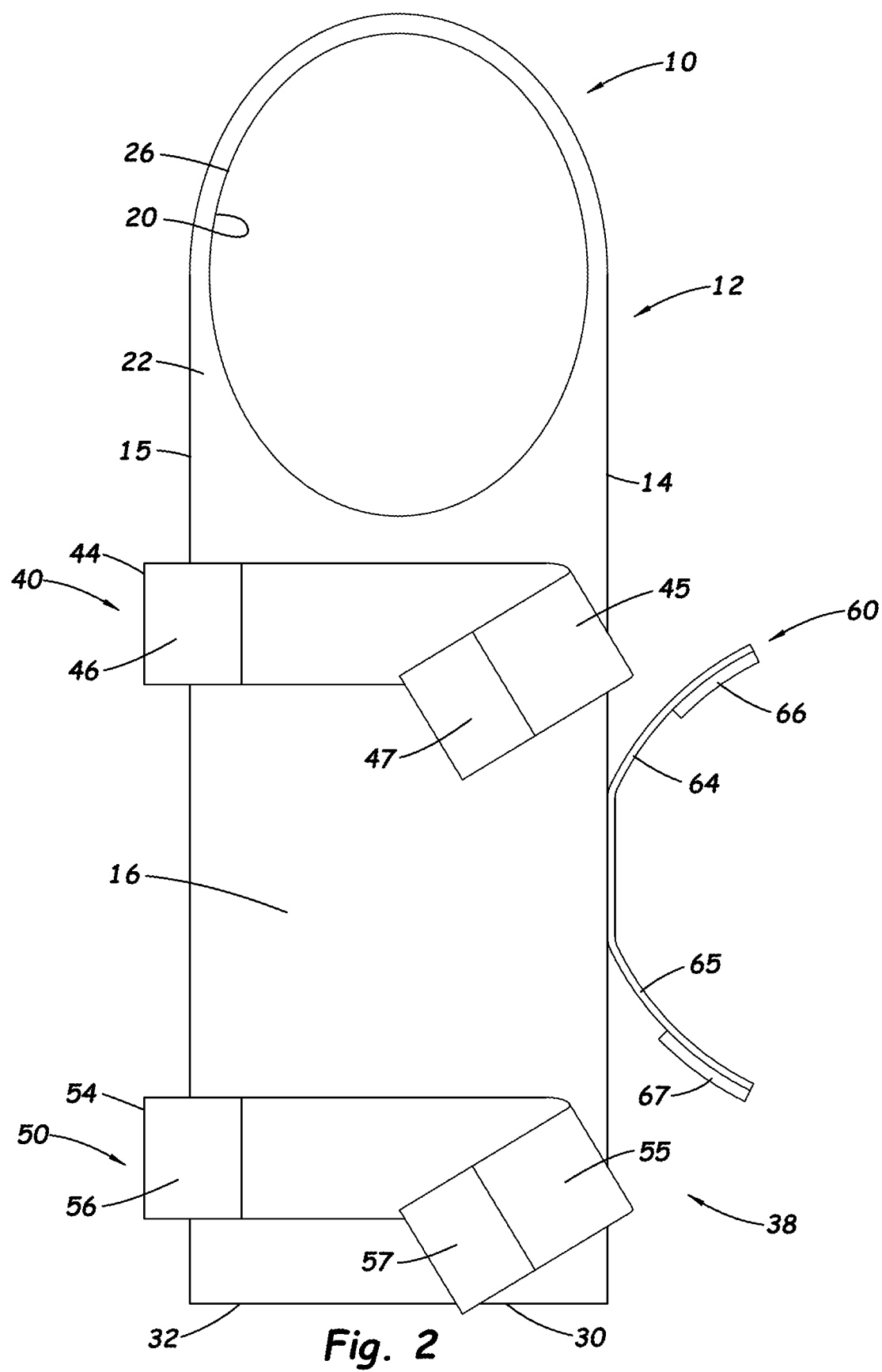
FIG. 2 is a schematic side view of the sling apparatus, according to an illustrative embodiment.
Figure 3A:
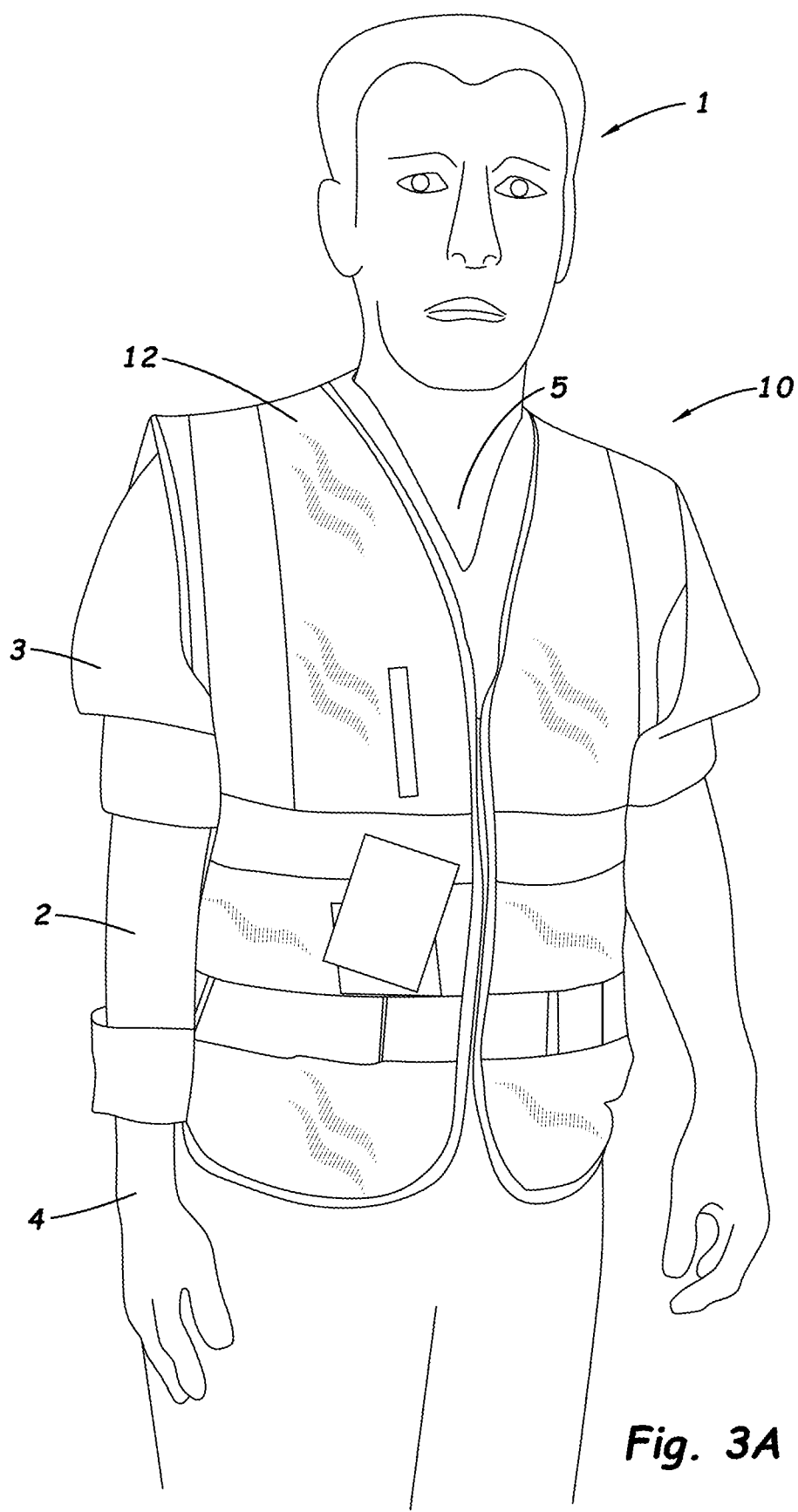
FIG. 3A is a schematic front view of the sling apparatus worn by a person and supporting an arm of the person in a first position.
Figure 3B:
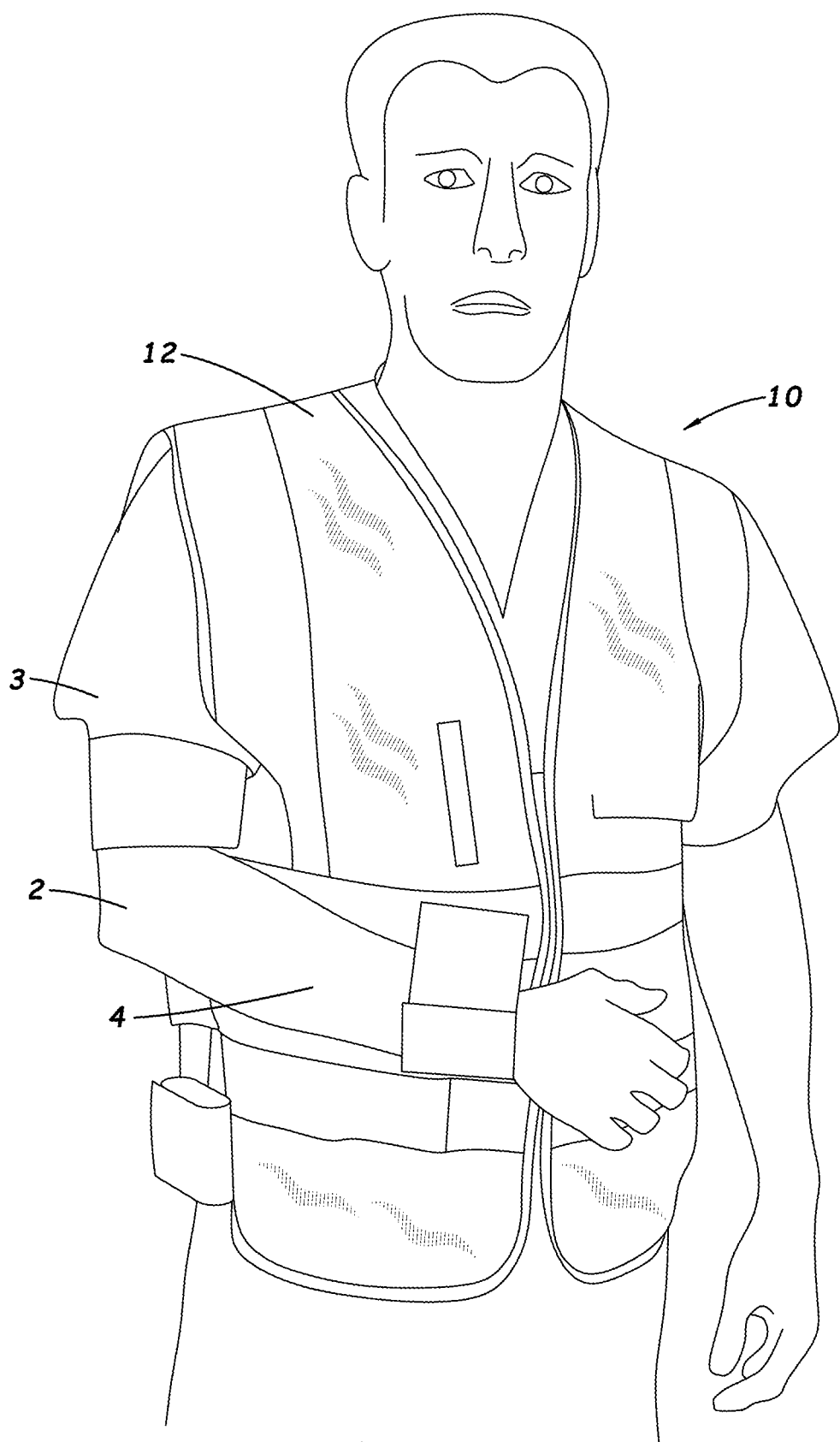
FIG. 3B is a schematic front view of the sling apparatus worn by a person and supporting the arm of the person in a second position.
Figure 3C:
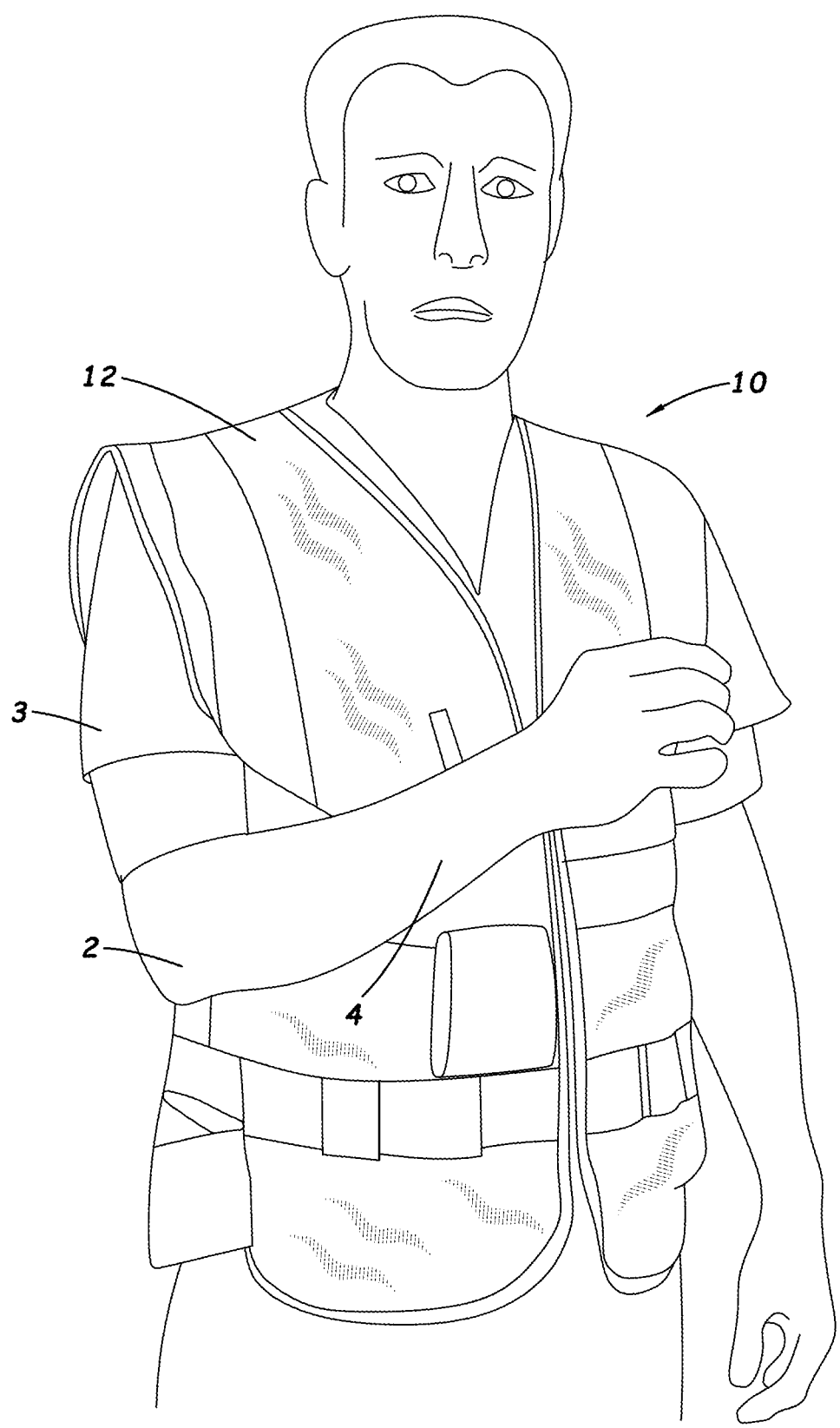
FIG. 3C is a schematic front view of the sling apparatus worn by a person and supporting the arm of the person in a third position.
Figure 4:
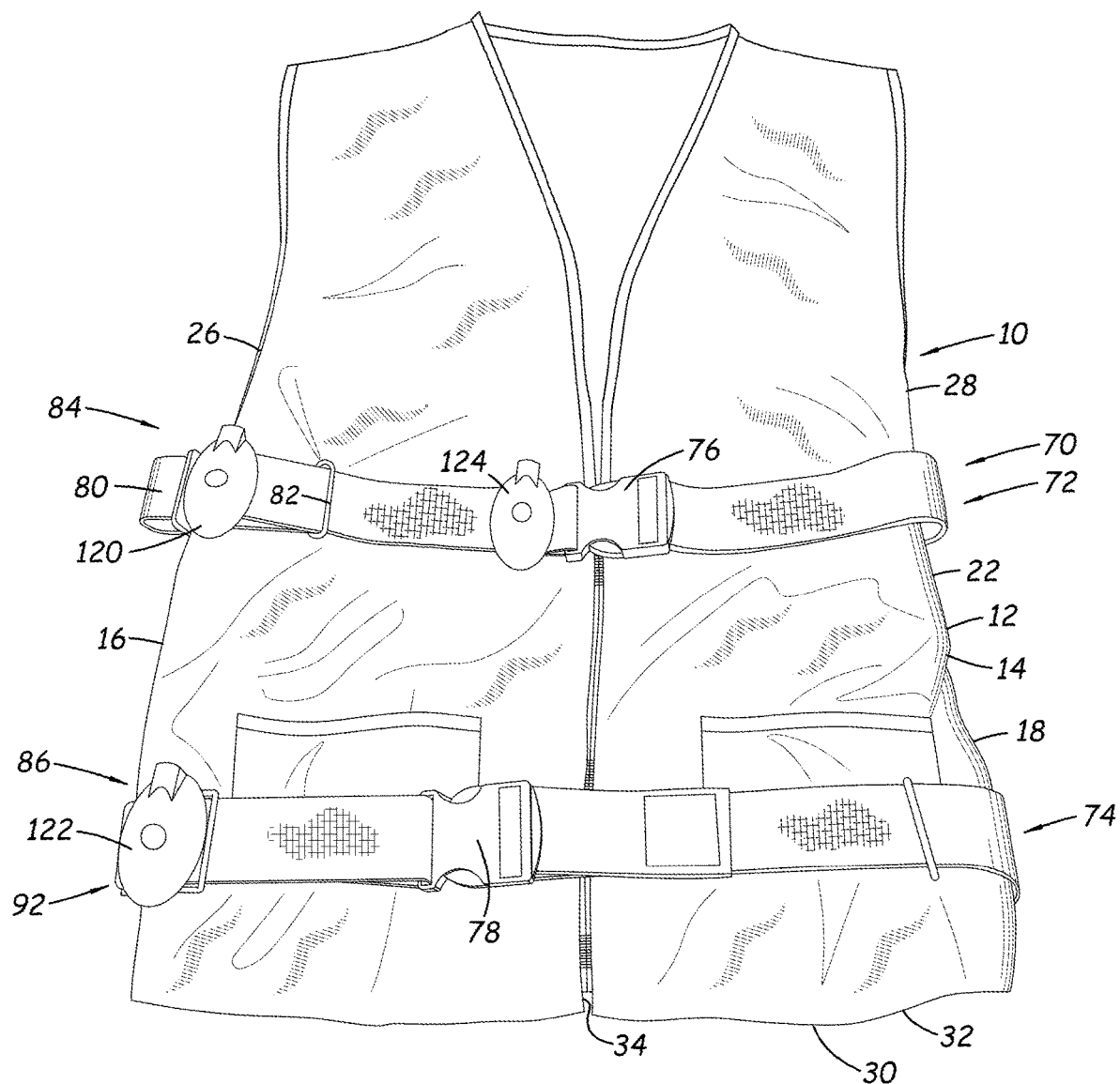
FIG. 4 is a schematic front view of elements of another illustrative embodiment of the new sling apparatus showing the cuff mounts without the cuffs, according to the present disclosure.
Figure 5A:
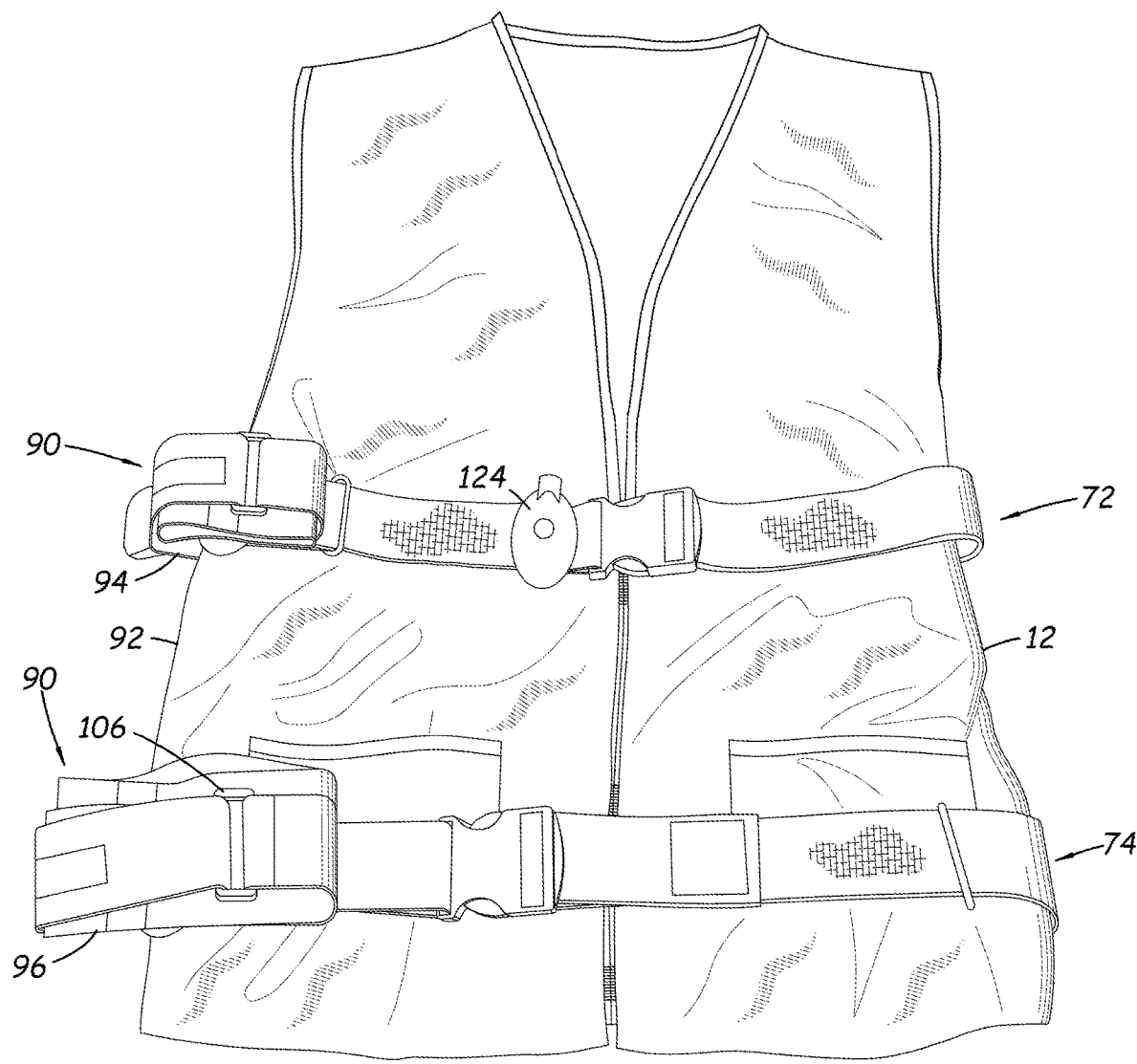
FIG. 5A is a schematic front view of the illustrative embodiment of the sling apparatus of FIG. 4 configured to be worn by a person for supporting an arm of the person in a first position.
Figure 5B:
FIG. 5B is a schematic front view of the illustrative embodiment of the sling apparatus of FIG. 4 configured to be worn by a person for supporting the arm of the person in a second position.
Figure 6:
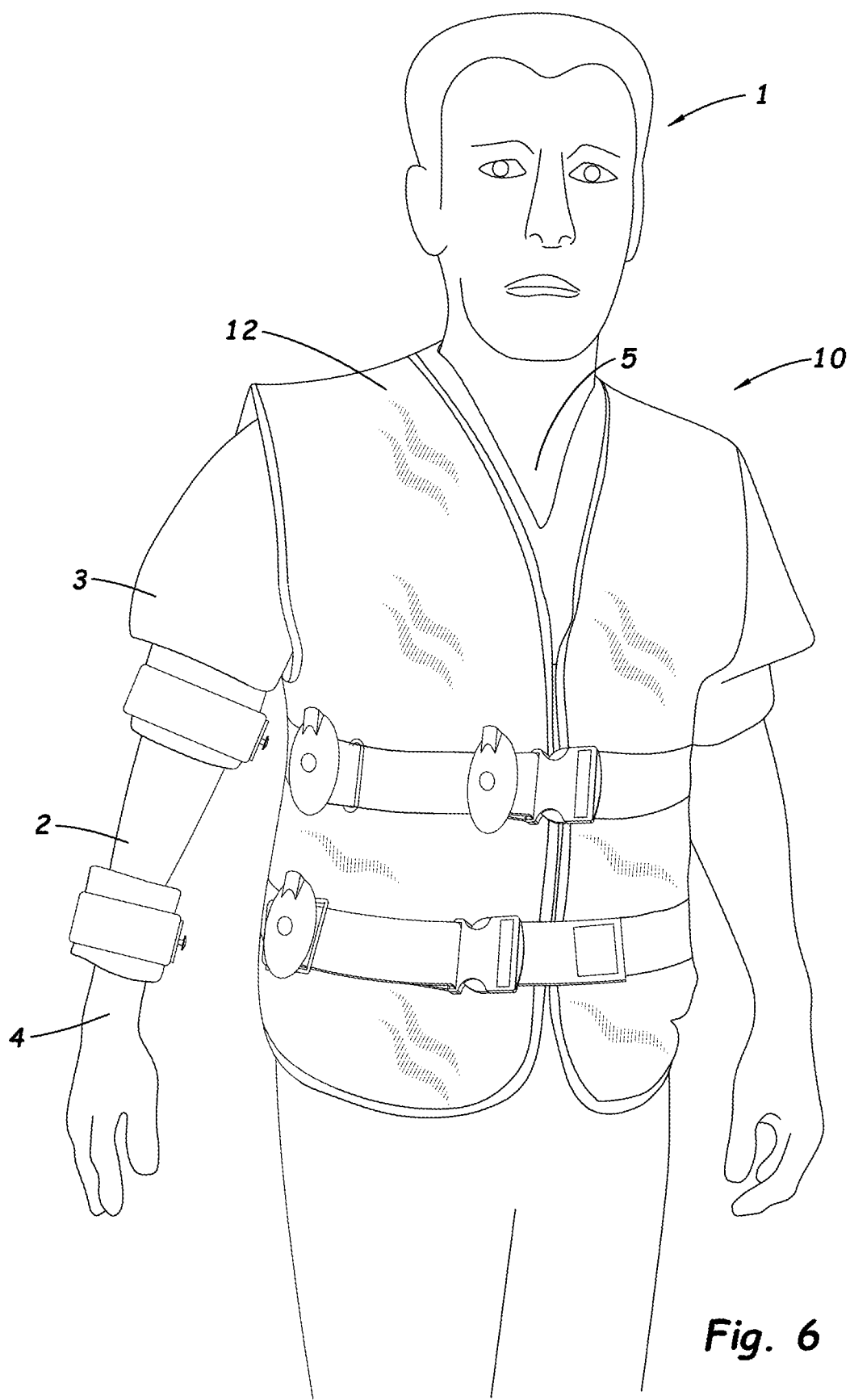
FIG. 6 is a schematic front view of the illustrative embodiment of the sling apparatus of FIG. 4 worn by a person with the cuffs of the apparatus shown dismounted from the cuff mounts.
Figure 7:
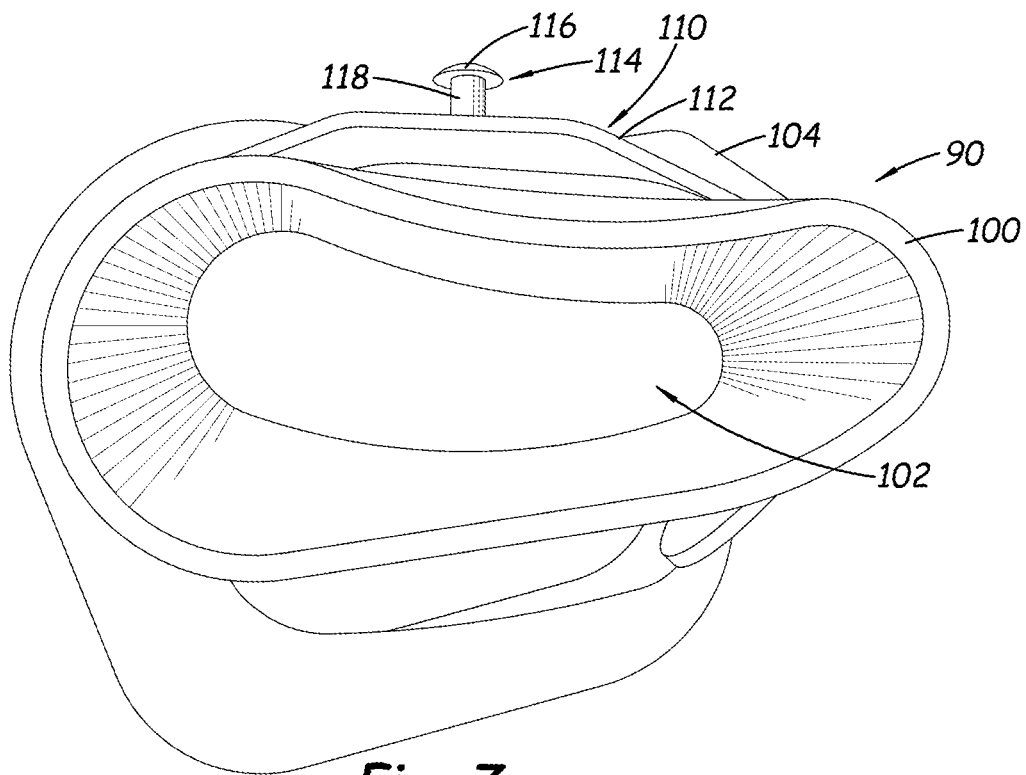
FIG. 7 is a schematic end view of the cuff of the illustrative embodiment of FIG. 4.
Figures 8A, 8B:
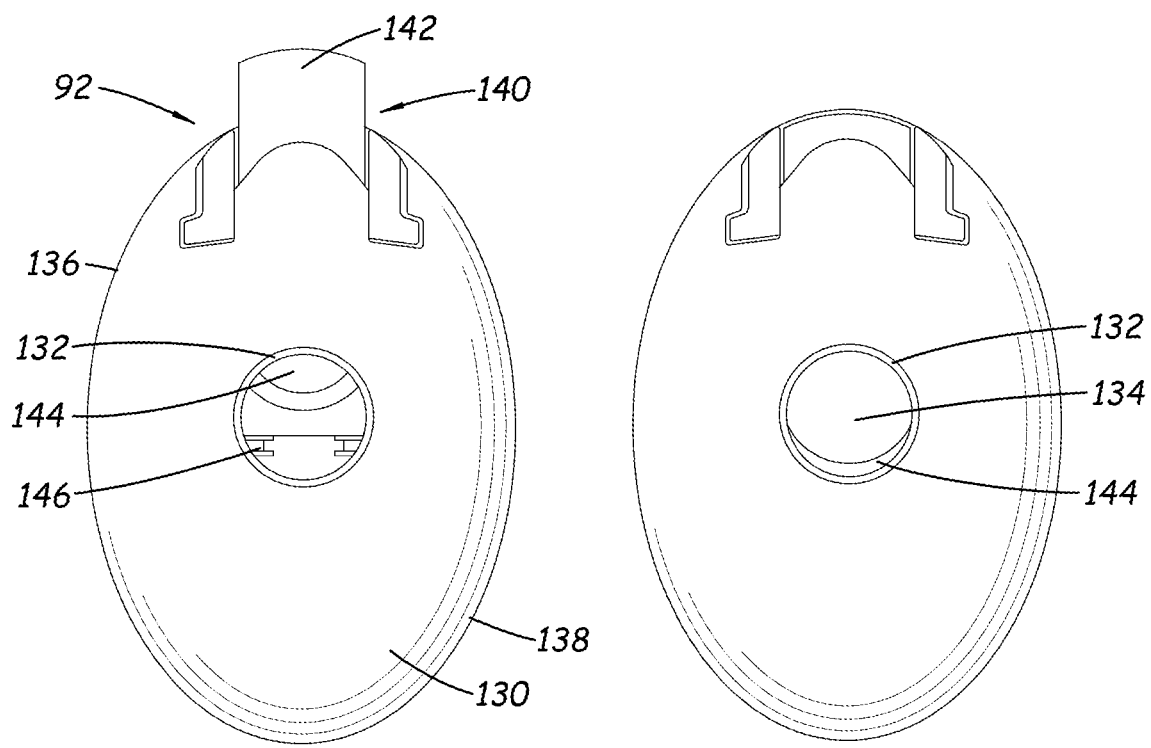
FIG. 8A is a schematic front view of the cuff mount of the illustrative embodiment of FIG. 4 in the latch position.
FIG. 8B is a schematic front view of the cuff mount of the illustrative embodiment of FIG. 4 in the release position.
Figure 9:
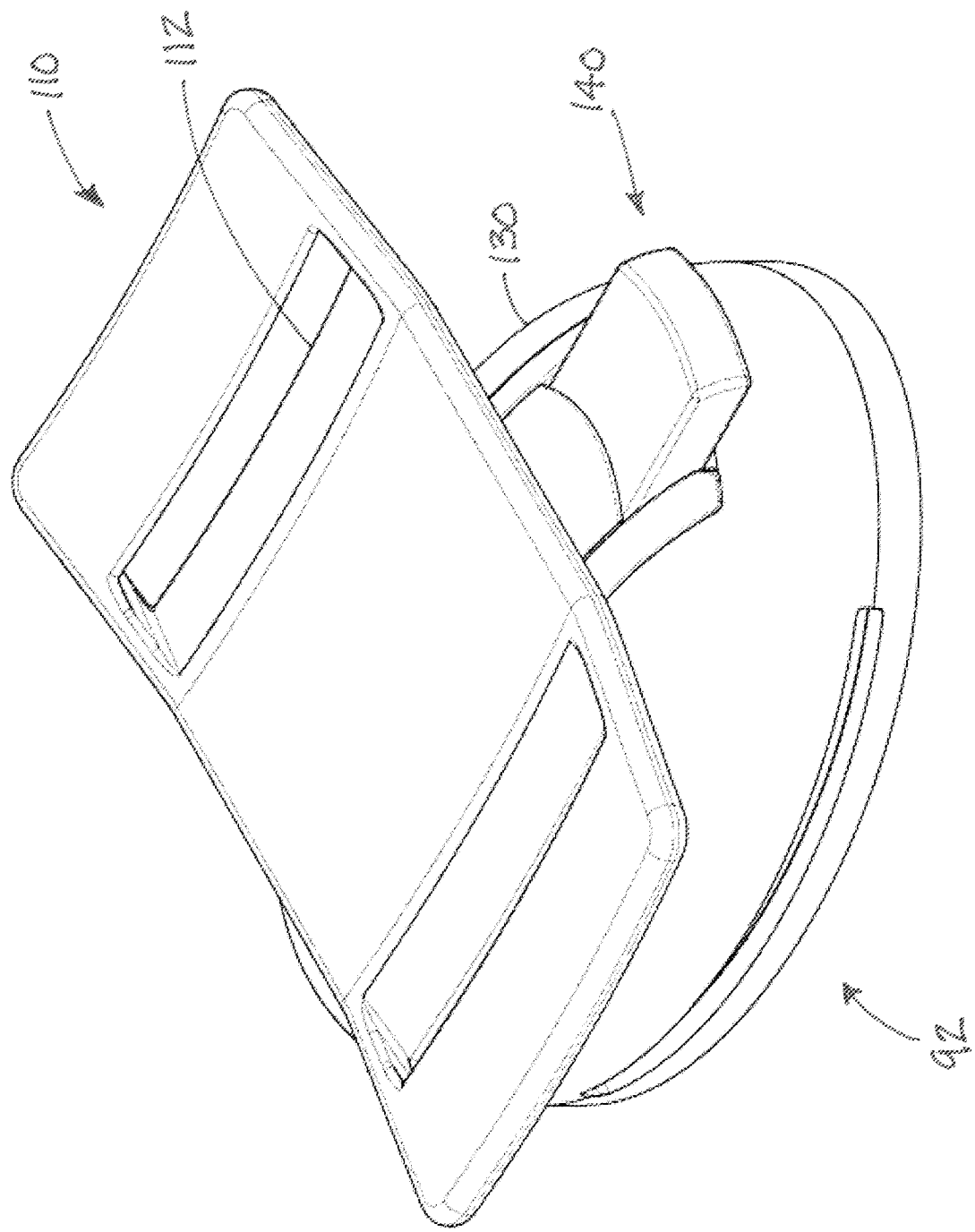
FIG. 9 is a schematic perspective view of the slider of the cuff (isolated from other elements of the cuff) and the housing of the cuff mount (isolated from other elements of the cuff mount) in a mounted condition, according to an illustrative embodiment.
Figure 10:
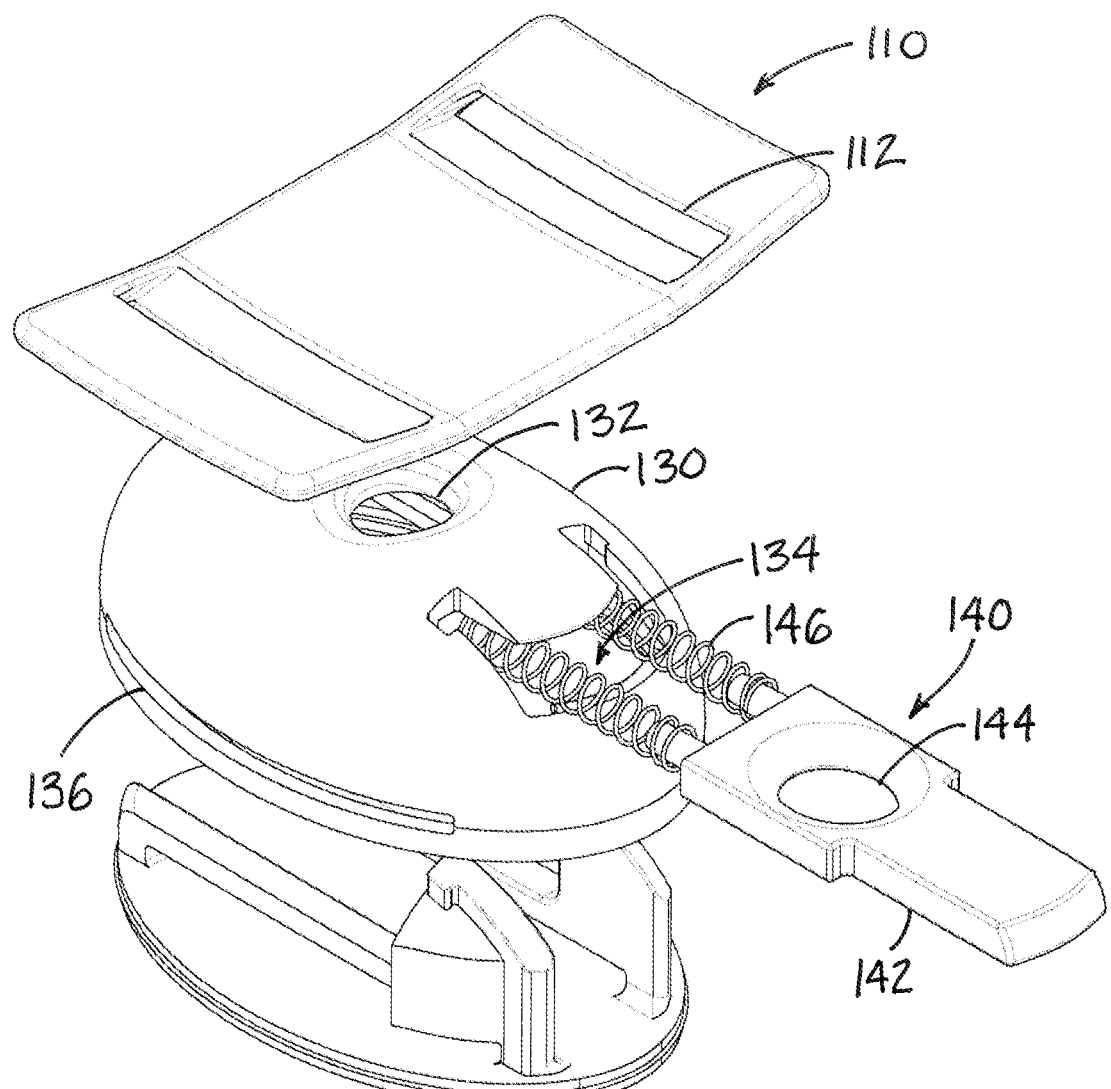
FIG. 10 is a schematic perspective exploded view of the slider of the cuff and elements of the cuff mount, according to an illustrative embodiment.
Figure 11:
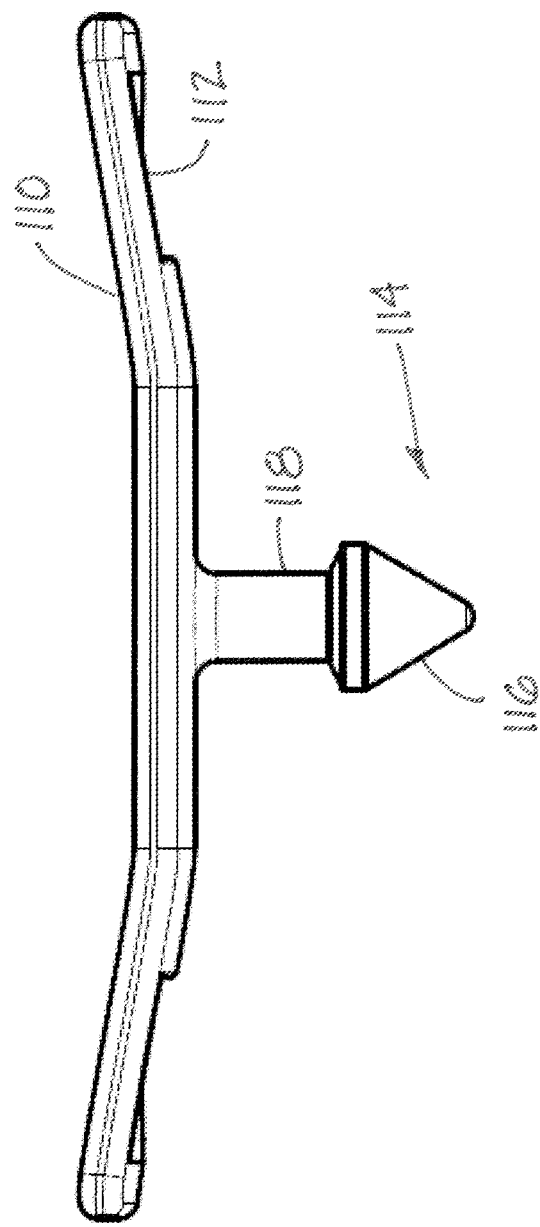
FIG. 11 is a schematic side view of the slider of the cuff, according to an illustrative embodiment.
Figure 12:
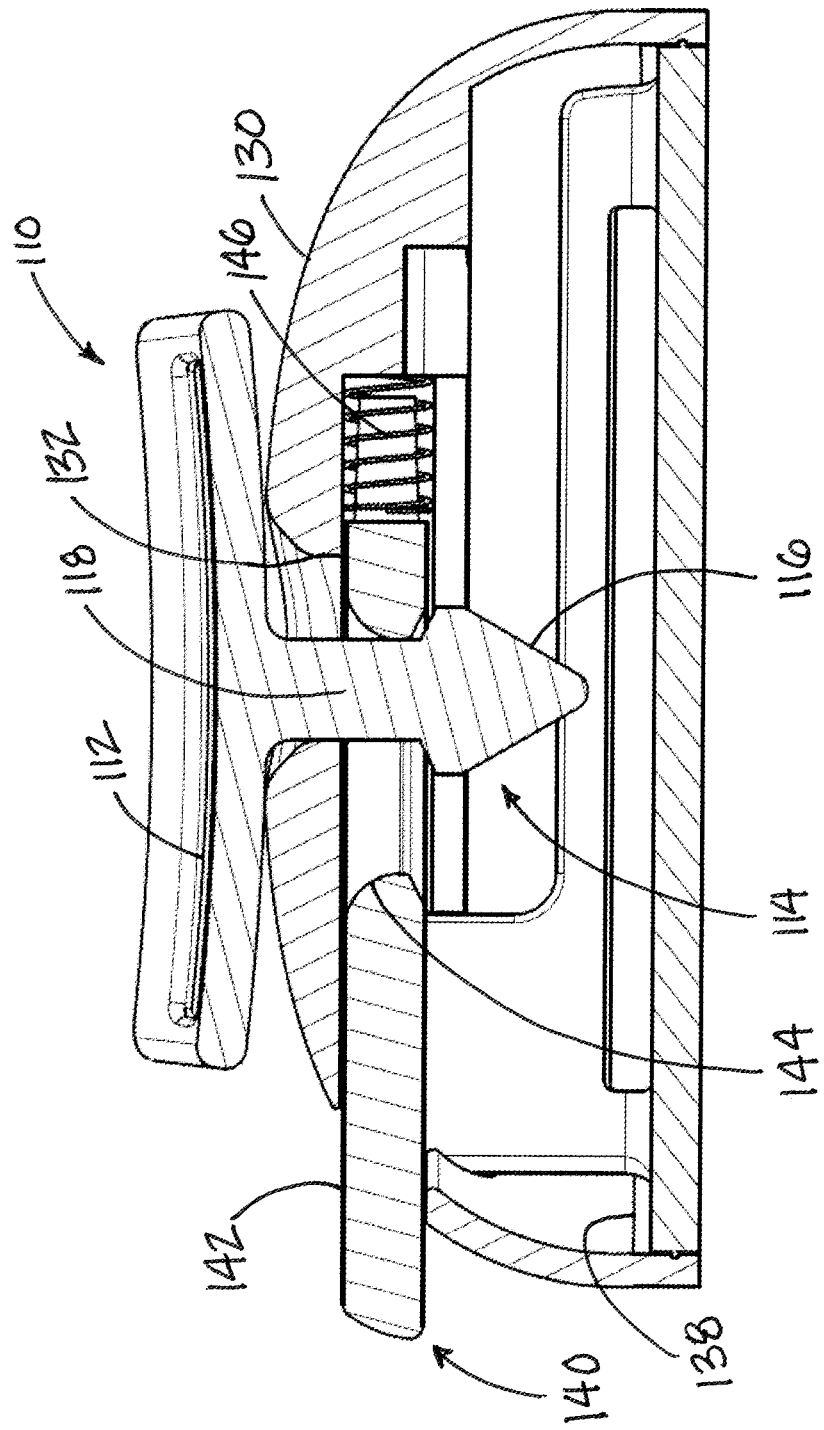
FIG. 12 is a schematic side sectional view of the slider of the cuff mounted on the cuff mount, according to an illustrative embodiment.

In some embodiments, such as those illustratively shown in FIGS. 1 through 3 of the drawings, the arm support elements 38 may include a plurality of loops which are integrally attached to the garment for removably receiving portions of the arm 2 that are desired to be supported by the apparatus 10. In addition to supporting portions of the arm, the plurality of loops may also constrain portions of the arm in each of the at least two positions.

The plurality of loops of the arm support elements 38 may include a first loop 40 which is configured for removably receiving the upper arm portion 3 of the arm of the person. The first loop 40 may be mounted on the outer surface 22 of the garment 12 and secured to the garment in any suitable manner, such as, for example, by sewing or otherwise bonding a portion of the loop 40 to the material of the garment. The first loop 40 may be positioned below a first one of the arm openings 26 of the garment, and may be positioned between the first arm opening and the lower edge 32 of the garment forming the torso opening 30. The first loop 40 may be positioned adjacent to the first arm opening 26 in a location suitable to receive the upper arm portion 3 of the person when the garment is worn by the person.

The first loop 40 may define a first passage 42 through which the upper arm portion 3 is insertable, and the first passage may extend along a substantially vertically-oriented axis when the garment 12 is worn by a standing person such that the upper arm portion 3 is held in a substantially vertical orientation in association with the torso 5.

In some embodiments, the first loop 40 may be configured to open to receive the upper arm portion 3 into, and release the upper arm portion from, the loop 40. The first loop 40 may also be configured to close to encircle and embrace the upper arm portion 3 to secure the arm portion 3 against movement out of the first loop. Illustratively, the first loop 40 may include a pair of first flaps 44, 45 which are joinable together to close the loop 40, and which are releasable from each other to open the loop 40. The first flaps 44, 45 may have connecting elements 46, 47 thereon to permit releasable connection of the first flaps together, as well as to permit release of the first flaps from each other. Optionally, the first connecting elements 46, 47 may comprise a hook and loop fasteners, such as fasteners sold under the VEL-CRO trademark.

The plurality of loops of the arm support elements 38 may further include a second loop 50 which is configured for removably receiving the lower arm portion 4 of the arm of the person. The second loop 50 may be mounted on the outer surface 22 of the garment 12 by securing the loop 50 to the garment using any suitable means. The second loop 50 may be positioned below one of the arm openings, such as the first arm opening 26 which has the first loop 40 positioned beneath it, and the loop 50 may be positioned between the arm opening 26 and the lower edge 32. The second loop 50 may also be positioned between the first loop 40 and the lower edge 32 at a location that is suitable for the second loop to receive the lower arm portion 4 of the arm 2 when the upper arm portion 3 is received by the first loop 40.

The second loop 50 may define a second passage 42 through which the lower arm portion 4 is insertable, and the second passage 52 may extend along a substantially vertically-oriented axis when the garment 12 is worn by a standing person such that the lower arm portion 4 is held in a substantially vertical orientation in association with the torso 5. The axes of the first passage 42 and second passage 52 may be substantially vertically aligned with each other when the garment 12 is worn by a standing person.

Like the first loop 40, the second loop 50 may also be configured to open and close. The second loop 50 may open to receive, and release, the lower arm portion 4, and may close to encircle and embrace the lower arm portion 4 to secure the arm portion 4 against movement out of the second loop. Illustratively, the second loop 50 may include a pair of second flaps 54, 55 which are joinable together to close the loop 50, and which are releasable from each other to open the loop 50. The second flaps 54, 55 may have connecting elements 56, 57 thereon to permit releasable connection of the second flaps together, as well as release of the second flaps from each other. Optionally, the second connecting elements 56, 57 may also comprise a hook and loop fasteners.

The arm support elements 38 may also include a third loop 60 which is configured for removably receiving the lower arm portion 4 of the arm of the person, typically as an alternative to the lower arm portion being received in the second loop 50. The third loop 60 may also be mounted on the outer surface 22 of the garment 12 by securing the loop 60 to the garment using a suitable technique.

The third loop 60 may be positioned on the front 14 of the garment 12 and may be positioned between the first lateral side 16 and the slit 34 of the garment. The third loop 60 may be positioned adjacent to the slit 34, and may also be positioned at a vertical level which is medial to, or intermediate between, the vertical levels of the first 40 and second 50 loops when the garment 12 is worn by a standing person. The third loop 60 may define a third passage 62 through which the lower arm portion of the person is insertable. The third passage 62 may extend along a substantially horizontal axis when the garment is worn by a standing person such that the lower arm portion 4 is held in a substantially horizontal orientation. The axis of the third passage 62 is thus oriented substantially perpendicular to the axes of the first 42 and second 52 passages of the respective loops.

Similar to the first and second loops, the third loop 60 may also be configured to be openable to receive, and be closable to encircle, the lower arm portion 4 to secure the arm portion 4 against movement out of the second loop. Illustratively, the third loop 60 may include a pair of third flaps 64, 65 which are joinable together to close the loop 60, and which are releasable from each other to open the loop 60. The third flaps 64, 65 may have connecting elements 66, 67 thereon to permit releasable connection of the third flaps together, as well as release of the third flaps from each other. Optionally, the third connecting elements 66, 67 may also comprise a hook and loop fasteners.

In the first position, the arm of the person may be engaged by the first loop 40 and the second loop 50 such that the upper arm portion is substantially vertically oriented and the lower arm portion is also substantially vertically oriented. In the second position, the arm of the person may be engaged by the first loop 40 and the third loop 60 such that the upper arm portion is substantially vertically oriented and the lower arm portion is substantially horizontally oriented. In a third position, the upper arm portion may be engaged by the first loop 40 but the lower arm portion may be free of engagement by the second and third loops, so that the forearm, wrist and hand are able to move relatively freely and the upper arm portion may rotate at the shoulder to facilitate the range of free movement by the lower arm portion.

In other embodiments, such as those illustratively shown in FIGS. 4 through 7, arm support elements may be supported on the garment by a garment cinching assembly 70 which is mounted on the garment 12 and is configured to cinch the garment against the torso of a person in a substantially snug relationship to the torso so that portions of the garment are held close to the body and the garment is not generally loose fitting on the torso. The garment cinching assembly 70 may be positioned along the outer surface 22 of the garment.

The garment cinching assembly 70 may include at least one garment cinching strap 72 which is configured to form a loop encircling a portion of the garment, as well as the torso of the person when the garment is worn by the person, to cinch the garment against the torso. The effective circumferential length of the loop formed by the garment cinching strap 70 may be adjustable such that the circumferential length may be decreased (or increased) in a manner that permits the strap to press against the garment and consequently press the garment against the torso of the person to control and typically greatly limit movement of the strap, as well as the garment, with respect to the torso. The garment cinching strap 70 may be positioned on the garment such that the loop formed by the strap 70 extends about the garment in a plane that is oriented substantially parallel to a plane defined by the lower edge 32 of the garment forming the torso opening 30.

In some embodiments, including some highly preferred embodiments, the garment cinching assembly 70 includes a pair of the garment cinching straps and includes an upper cinching strap 72 positioned relatively closer to the neck opening 24 of the garment and a lower cinching strap 74 positioned relatively closer to the torso opening 34 to snug the encircled portions of the garment against the respective portions of the torso. An upper buckle 76 may selectively connect portions of the upper cinching strap and a lower buckle 78 may selectively connect portions of the lower cinching strap. The upper 76 and lower 78 buckles may be positioned generally proximate to the slit 34 of the garment. The position of the upper buckle 76 on the upper cinching strap 72 may be adjustable to adjust the effective circumferential length of the upper cinching strap to permit the cinching strap to be snugged up to the torso of the person, and similarly the position of the lower buckle 78 on the lower cinching strap 74 may be adjustable to adjust the effective circumferential length of the lower cinching strap to permit the cinching strap to be snugged up to the torso of the person.

The garment cinching assembly 70 may further include a plurality of support rings 80, 82 which is mounted on the garment 12 and configured to support one of the garment cinching straps on the garment. The plurality of support rings 80, 82 may be positioned on the outer surface 22 of the garment to support the strap along the outer surface, In embodiments having upper and lower cinching straps, a group of the support rings may be provided for each of the straps, and the support rings of a group may be arranged along a line that extends substantially parallel to the torso opening 30, and the lower edge 32, of the garment.

Each group of support rings may include at least one pair 84, 86 of the support rings to support a section of the respective cinching strap on the garment. Illustratively, each group of support rings may include at least two pair of support rings, and the pair of support rings of a group may be positioned on opposite side regions of the garment 12, such as on respective lateral sides 16, 18 of the garment. The support rings of each pair may be spaced along the line extending substantially parallel to the torso opening, and as a result the cinching straps may be supported on the torso in a substantially horizontal orientation when worn by a person standing upright. The support rings 80, 82 may form the only connection of the cinching straps 72, 74 to the garment to permit substantially free movement of the cinching straps with respect to the garment when, for example, the straps are snugged or contracted against the garment and the torso.

In the embodiments shown in FIGS. 4 through 7, the arm support elements may include a plurality of cuffs 90 for receiving portions of the arm of the person to support the arm in each of the two positions, and may also include a plurality of cuff mounts 92 supported on the garment cinching assembly 70 that are configured to movably mount the cuffs 90 on the cinching assembly 70. Each of the cuffs 90 may each be removably mounted on one of the cuff mounts 92 in a mounted condition of the respective cuff, and may be removed from the mounted condition on the cuff mount in a dismounted condition of the respective cuff. The plurality of cuff mounts 92 may each be mounted on one of the cinching straps of the cinching assembly 70, and each cuff mount may be adjustably positionable along at least a portion of one of the cinching straps. Illustratively, each of cuff mounts 92 may be slidable along a portion of a cinching strap. In some embodiments, one or more of the cuff mounts 92 may be positioned between a pair of the support rings 84, 86 to provide a degree of restriction on the movement of the cuff mount along the cinching strap on which the mount 92 is mounted.

The plurality of cuffs 90 may include an upper arm cuff 94 for receiving the upper arm portion 3 of the arm 2 of the person and a lower arm cuff 96 for receiving the lower arm portion 4 of the arm of the person. In greater detail, each of the cuffs 94, 96 may include a sleeve 100 which may define a passage 102 through which a portion of the arm of the person is insertable. The sleeve 100 may be tubular and substantially continuous about the passage 102 to encircle the arm portion, although a non-continuous sleeve may be employed. Illustratively, the sleeve 100 may be formed of a compressible material for enhanced comfort against the flesh of the arm portion, and the material of the sleeve may also be elastomeric in character. Optionally, the sleeve 100 may have enhanced padding at selected contact points. The arm cuffs 94, 96 may each further include a band 104 extended about the sleeve 100, and the band may have an adjustable effective circumferential length to permit constriction of the band against the sleeve to constrict the sleeve about the arm portion of the arm of the person. A cinching loop 106 may be mounted on one end of the band for receiving an opposite end portion of the band to permit the band to be cinched against the sleeve, and the band may have connecting elements positioned thereon to releasably connect portions of the band together to adjust the effective circumferential length of the band. Illustratively, the connecting elements may comprise hook and loop fasteners, although other connecting elements may be utilized. Each cuff may further include a slider 110 for mounting on the band 104, and the slider may have at least one slot 112 through which a portion of the band passes. Typically, the slider 110 has a pair of the slots, and movement of the strap through the slot or slots requires overcoming a degree of resistance to the movement that facilitates the slider holding its positioned along the strap. The slider 110 may have a nub 114 or protuberance. In the illustrative embodiments, the nub 114 may have a mushroom shape, with a relatively wider head 116 and a relatively narrower stalk 118. and optionally other configurations may be suitable.

The plurality of cuff mounts 92 may include an upper cuff mount 120 which may be mounted on and supported by the upper cinching strap 72, a lower cuff mount 122 which may be mounted on and supported by the lower cinching strap 74, and a forward cuff mount 124 which may be mounted on and supported by the upper cinching strap 72. The upper cuff mount 120 and the lower cuff mount 122 may be positioned on the respective upper and lower cinching straps at locations on the straps generally adjacent to the same lateral side of the garment (and adjacent to the side region of the outer surface of the garment below the respective arm opening) depending upon the specific arm of the person to be supported. In some implementations, the upper cuff mount 120 and a lower cuff mount 122 may be positioned between respective pairs of support rings supporting the upper and lower cinching straps to provide a degree of confinement of movement of the cuff mounts along the respective straps. The forward cuff mount 124 may be positioned on the upper cinching strap at a location adjacent to the front region of the garment, typically adjacent to the slit 34 of the garment.

In some embodiments, each of the cuff mounts 92 may comprise a housing 130 which may have an aperture 132 for receiving a portion of the nub 114 of the slider 110 of one of the cuffs. The housing 130 may define an interior 134 into which a portion of the nub may be inserted after passing through the aperture 132. The housing 130 may have a slit 136 through which a portion of one of the cinching straps passes to mount the housing on the strap. Typically, the housing has a pair 136, 138 of the slits. In the illustrative embodiments, the housing 130 may be formed by an upper portion and a lower portion, with the aperture 132 and the slits 136, 138 being formed in the upper portion of the housing Each of the cuff mounts 92 may also comprise a latching mechanism 140 which in some of the most preferred embodiments permits the cuff 90 to be mounted on the cuff mount 92 without requiring manual manipulation of the cuff mount by the person wearing the apparatus 10, and may require manual manipulation of the cuff mount by the person wearing the apparatus to release the cuff from the cuff mount. Illustratively, the latching mechanism 140 may be configured so that pressing of the cuff 90 against the cuff mount 92 can mount the cuff on the cuff mount, while the latching mechanism 140 resists dismounting of the cuff from the cuff mount unless manual intervention or manipulation of the latching mechanism of the cuff mount is performed. The latching mechanism 140 is mounted on the housing 130 and may be positioned in the interior 134 of the housing. The latching mechanism 140 may be configured to engage a nub 114 which is extended through the aperture 132 in the housing. In some embodiments, the latching mechanism 140 may comprise a latch member 142 which is at least partially positioned in the interior 134 of the housing. The latch member 142 may be movable with respect to the housing 130 between a latch position and a release position. The latch position of the latch member may be characterized by the latch member engaging the nub 114 and resisting removal of the nub from the housing, and the release position of the latch member may be characterized by the latch member permitting removal of the nub from the housing. The release position may further be characterized by the latch member permitting insertion of the nub into the housing. Illustratively, the latch member 142 may define a recess 144 for removably receiving the nub 114. The recess 144 may be in relatively greater alignment with the aperture 132 of the housing in the release position to permit the head of the nub to easily pass through both the aperture into the recess. In the latch position, the recess may be in relatively lesser alignment with the aperture 132 of the housing such that the head of a nub positioned in the recess is unable to move through the aperture. Illustratively, the shape of the head 116 of the nub 114, such as a generally pointed conical shape, may facilitate the penetration of the nub through the aperture 132 of the housing and engagement of the head of the nub with the recess 144 of the latch member to cause displacement or movement of the latch member from the latch position toward the release position and permit the head to move through the recess 144 so that the latch member moves back toward the latch position as the stalk 118 of the nub moves into the recess.

In some embodiments, a portion of the latch member 142 may protrude from the interior 134 of the housing 132 to an exterior location to permit manual manipulation of the position of the latch member by the hand of the person, such as to move the latch member from the latch position toward the release position. In the illustrative embodiments, the latch member 142 extends through a slot formed in the upper portion of the housing 132 in a location which is convenient for access to the latch member when the slider 110 of the cuff 90 is mounted on the cuff mount 92. The latching mechanism 140 may further include a biasing element 146 which is configured to bias the latch member toward the latch position. The biasing element 146 may be positioned in the interior of the housing, and illustratively may comprise a compression spring positioned between a surface on the interior of the housing and the latch member, although other biasing elements or means may be utilized. In the illustrative embodiments, a pair of compression springs may be utilized. Thus, manipulation of the latch member 142 may be needed only to move the latch member from the latch position to the release position to release the nub from the latch member by producing sufficient alignment of the recess 144 with the aperture 132 to permit the head 116 of the nub to move out of the recess and the aperture so that the cuff is dismounted from the cuff mount.

The upper arm cuff 94 may be mounted on the upper cuff mount 120 to provide any of the three positions of the arm, and may also be dismounted from the upper cuff mount to facilitate removal of the cuff from the arm of the person as well as other tasks. The lower arm cuff 96 may be mounted on the lower cuff mount 122 in the first position of the arm (see, e.g., FIG. 5A), and may be mounted on the forward cuff mount 124 in the second position of the arm (see, e.g., FIG. 5B), or optionally the lower arm cuff may be completely free of attachment to any of the cuff mounts to provide the third position of the arm.

Advantageously, the removable mounting of the cuffs on the cuff mounts provides the ability to support the arm in the first and second positions without having to provide separate cuffs for each of the first and second positions. Thus, as a result of the ability to move the lower arm cuff 96 between the lower cuff mount 122 and the forward cuff mount 124, only a single lower arm cuff is needed to provide support for the lower arm portion of the person in both the first and second positions. Also, switching of the arm between the first and second positions is made easier as the lower arm cuff merely needs to be released from one of the two cuff mounts and engaged with the other one of the two cuff mounts without having to remove the arm portion from one cuff and then place the arm portion in another cuff. Further, the configuration of the nub 114 on the slider 110 of a cuff 90 may permit a degree of rotation of the cuff with respect to the cuff mount to provide a more comfortable orientation of the cuff with respect to the cuff mount (and the garment cinching assembly) than may be possible with a more permanent mounting of the cuff on the respective cinching strap.

Optionally, embodiments of the arm support elements may utilize cuffs which are directly and inseparably mounted on the garment cinching assembly, in contrast to the removable mounting of the cuffs in the embodiments shown in FIGS. 4 through 7 and also in contrast to the direct mounting of the loops on the garment itself in the embodiments shown in FIGS. 1 through 3. Such optional embodiments may involve the direct mounting of the cuffs on the respective cinching straps by, for example, sewing or other means of relatively permanent attachment, and such embodiments may require that a cuff be provided for supporting the lower arm portion in each of the first and second positions, and thus a lower arm cuff may need to be provided on both the upper and lower cinching straps at the appropriate locations along the straps to produce the first and second positions of the arm.

It should be appreciated that in the foregoing description and appended claims, that the terms "substantially" and "approximately," when used to modify another term, mean "for the most part" or "being largely but not wholly or completely that which is specified" by the modified term.

It should also be appreciated from the foregoing description that, except when mutually exclusive, the features of the various embodiments described herein may be combined with features of other embodiments as desired while remaining within the intended scope of the disclosure.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated.

With respect to the above description then, it is to be realized that the optimum dimensional relationships for the parts of the disclosed embodiments and implementations, to include variations in size, materials, shape, form, function and manner of operation, assembly and use, are deemed readily apparent and obvious to one skilled in the art in light of the foregoing disclosure, and all equivalent relationships to those illustrated in the drawings and described in the specification are intended to be encompassed by the present disclosure.

Therefore, the foregoing is considered as illustrative only of the principles of the disclosure. Further, since numerous modifications and changes will readily occur to those skilled in the art, it is not desired to limit the disclosed subject matter to the exact construction and operation shown and described, and accordingly, all suitable modifications and equivalents may be resorted to that fall within the scope of the claims.

I claim:

1. A sling apparatus for supporting an arm of a person with respect to a torso of the person, the arm including an upper arm portion and a lower arm portion, the sling apparatus comprising:

a vest garment configured to be worn on the torso of the person, the vest garment having a neck opening configured for receiving the neck of the person, the vest garment having a torso opening opposite of the neck opening for receiving a portion of the torso of the person, the torso opening being formed by a lower edge of the vest garment, the vest garment having a pair of arm openings fer each configured for receiving an arm of the person, the vest garment having a front extending from the neck opening to the torso opening for positioning adjacent to a front of the torso, a back extending from the neck opening to the torso opening for positioning adjacent to a back of the torso, and a pair of lateral sides each extending from a respective one of the arm openings to the torso opening and each extending between the front and back of the vest garment for positioning adjacent to a side of the torso;

a garment cinching assembly mounted on the vest garment to cinch about the torso of a person, the garment cinching assembly comprising a pair of cinching straps each extending about the vest garment in an orientation substantially parallel to the lower edge of the vest garment, the pair of cinching straps including an upper cinching strap positioned further away from the lower edge of the vest garment and a lower cinching strap positioned closer to the lower edge of the vest garment forming the torso opening: and arm support elements configured to support the arm of the person wearing the vest garment in at least two positions with respect to the torso, the at least two positions including a first position of the arm having the elbow extended with a shoulder associated with the arm of the person being in a neutral rotation orientation and a second position of the arm with the elbow flexed and the shoulder associated with the arm being in an adducted, internal rotation position;

wherein a first one of the arm support elements is configured to support the upper arm portion of the person on the vest garment and a second one of the arm support elements is configured to support the lower arm portion of the person on the vest garment;

wherein the first one of the arm support elements includes:

an upper cuff mount mounted on the upper cinching strap and positioned adjacent to a first one of the lateral sides of the vest garment; and an upper arm cuff for receiving the upper arm portion of the arm of the person, the upper arm cuff being removably mounted on the upper cuff mount: wherein the second one of the arm support elements includes:

a lower arm cuff for receiving the lower arm portion of the arm of the person: a lower cuff mount mounted on the lower cinching strap and positioned at a first location adjacent to the first one of the lateral sides of the vest garment;

a forward cuff mount mounted on the upper cinching strap and positioned at a second location adjacent to the front of the vest garment, the second location on the vest garment being different than the first location on the vest garment; and wherein the first location corresponds to a location of the lower arm cuff when the arm of the person is in the first position and the second location corresponds to a location of the lower arm cuff when the arm of the person is in the second position;

wherein the lower arm cuff of the second one of the arm support elements is mountable on and dismountable from each of the lower cuff mount and the forward cuff mount individually and independently of the first one of the support elements to permit interchangeable mounting of the lower arm cuff of the second one of the arm support elements to the vest garment in the first and second locations on the vest garment.

2. The apparatus of claim 1 wherein each cuff mount of the first one and the second one of the arm support elements comprises:

a housing mounted on one of the pair of cinching straps of the garment cinching assembly, the housing having an aperture for receiving a portion of a nub of one of the cuffs; and a latching mechanism mounted on the housing and being configured to engage a said nub extending through the aperture in the housing.

3. The apparatus of claim 2 wherein the latching mechanism comprises a latch member mounted on the housing, the latch member being movable with respect to the housing between a latch position and a release position, the latch position being characterized by the latch member being configured to engage the nub of a cuff inserted into the aperture of the housing and resist removal of the nub from the housing, the release position being characterized by the latch member permitting removal of the nub of a cuff from the aperture of the housing.

4. The apparatus of claim 3 wherein the latching mechanism comprises a biasing element configured to bias the latch member toward the latch position.

5. The apparatus of claim 1 wherein the lower cuff mount is slidably positionable along the lower cinching strap to set a position of the first location of the lower cuff mount adjacent to the first one of the lateral sides of the vest garment.

6. The apparatus of claim 5 wherein the forward cuff mount supported on the upper cinching strap forward cuff mount is slidably positionable along the upper cinching strap to set a position of the second location of the lower cuff mount adjacent to the front of the vest garment.

7. The apparatus of claim 1 wherein the at least two positions include a third position of the arm having the upper arm portion constrained on the vest garment in a position configured to be adjacent to the torso and the lower arm portion unconstrained by the second one of the arm support elements.

8. The apparatus of claim 1 wherein the upper cuff mount of the first one of the arm support elements and the lower cuff mount and the forward cuff mount of the second one of the arm support elements are each adjustably positionable along a respective one of the cinching straps.

9. The apparatus of claim 1 wherein each of the garment cinching straps of the garment cinching assembly has an adjustable effective circumferential length to permit cinching of the cinching strap about the torso of the person.

10. The apparatus of claim 1 wherein the lower cinching strap is positioned on the vest garment at a location spaced from the lower edge of the vest garment toward the pair of arm openings and the upper cinching strap is positioned on the vest garment at a location spaced from the pair of arm openings toward the lower edge of the vest garment.

11. The apparatus of claim 1 wherein the first location of the lower cuff mount is located on the vest garment between the location of the upper cuff mount and the torso opening and the second location of the forward cuff mount is located on the vest garment between the neck opening and the torso opening.

12. The apparatus of claim 1 wherein the second one of the arm support elements includes a latching mechanism configured to mount the lower arm cuff to the lower cuff mount or the forward cuff mount upon pressing of the lower arm cuff against the lower cuff mount or the forward cuff mount, the latching mechanism resisting dismounting of the lower arm cuff from the lower cuff mount or the forward cuff mount unless the latching mechanism is manually manipulated by pressing on a member of the latching mechanism.

13. The apparatus of claim 1 wherein each cuff mount of the first one and the second one of the arm support elements is slidable along a respective one of the garment cinching straps.

14. The apparatus of claim 1 wherein each cuff of the first one and the second one of the arm support elements comprises :
a sleeve configured to receive a portion of the arm of the person;
a band extended about the sleeve, the band having an adjustable effective circumferential length to permit constriction of the band and the sleeve about the portion of the arm of the person; and
a slider receiving a portion of the band, the slider having a nub.

15. A sling apparatus for supporting an arm of a person with respect to a torso of the person, the arm including an upper arm portion and a lower arm portion, the sling apparatus comprising:
a vest garment configured to be worn on the torso of the person, the vest garment having a neck opening configured for receiving the neck of the person, the vest garment having a torso opening opposite of the neck opening for receiving a portion of the torso of the person, the torso opening being formed by a lower edge of the vest garment, the vest garment having a pair of arm openings each configured for receiving an arm of the person, the vest garment having a front extending from the neck opening to the torso opening for positioning adjacent to a front of the torso, a back extending from the neck opening to the torso opening for positioning adjacent to a back of the torso, and a pair of lateral sides each extending from a respective one of the arm openings to the torso opening and each extending between the front and back of the vest garment for positioning adjacent to a side of the torso;
a garment cinching assembly mounted on the vest garment to cinch about the torso of a person, the garment cinching assembly comprising a pair of cinching straps each extending about the vest garment in an orientation substantially parallel to the lower edge of the vest garment, the pair of cinching straps including an upper cinching strap positioned further away from the lower edge of the vest garment and a lower cinching strap positioned closer to the lower edge of the vest garment forming the torso opening, each of the garment cinching straps having an adjustable effective circumferential length to permit cinching of the cinching strap on the vest garment to press the garment against the torso of the person; and
arm support elements configured to support the arm of the person wearing the vest garment in at least two positions with respect to the torso, the at least two positions including a first position of the arm having the elbow extended with a shoulder associated with the arm of the person being in a neutral rotation orientation and a second position of the arm with the elbow flexed and the shoulder associated with the arm being in an adducted, internal rotation position;
wherein a first one of the arm support elements is configured to support the upper arm portion of the person on the vest garment and a second one of the arm support elements is configured to support the lower arm portion of the person on the vest garment;
wherein the first one of the arm support elements includes:
an upper cuff mount mounted on and slidable along the upper cinching strap to position the upper cuff mount adjacent to a first one of the lateral sides of the vest garment; and
an upper arm cuff for receiving the upper arm portion of the arm of the person, the upper arm cuff being removably mounted on the upper cuff mount;
wherein the second one of the arm support elements includes:
a lower arm cuff for receiving the lower arm portion of the arm of the person;
a lower cuff mount mounted on and slidable along the lower cinching strap to position the lower cuff mount at a first location adjacent to the first one of the lateral sides of the vest garment, the first location of the lower cuff mount being located on the vest garment between the location of the upper cuff mount on the vest garment and the torso opening;
a forward cuff mount mounted on and slidable along the upper cinching strap to position the forward cuff mount at a second location adjacent to the front of the vest garment, the second location on the vest garment being different than the first location on the vest garment; and
wherein the first location corresponds to a location of the lower arm cuff when the arm of the person is in the first position and the second location corresponds to a location of the lower arm cuff when the arm of the person is in the second position;
wherein the lower arm cuff of the second one of the arm support elements is mountable on and dismountable from each of the lower cuff mount and the forward cuff mount individually and independently of the first one of the support elements to permit interchangeable mounting of the lower arm cuff of the second one of the arm support elements to the vest garment in the first and second locations on the vest garment.

16. The apparatus of claim 15 wherein each cuff mount of the first one and the second one of the arm support elements comprises:
a housing mounted on one of the pair of cinching straps of the garment cinching assembly, the housing having an aperture for receiving a portion of a nub of one of the cuffs; and
a latching mechanism mounted on the housing and being configured to engage a said nub extending through the aperture in the housing.

17. The apparatus of claim 16 wherein the latching mechanism comprises a latch member mounted on the housing, the latch member being movable with respect to the housing between a latch position and a release position, the latch position being characterized by the latch member being configured to engage the nub of a cuff inserted into the aperture of the housing and resist removal of the nub from the housing, the release position being characterized by the latch member permitting removal of the nub of a cuff from the aperture of the housing.

18. The apparatus of claim 17 wherein the latching mechanism comprises a biasing element configured to bias the latch member toward the latch position.

19. The apparatus of claim 15 wherein the second one of the arm support elements includes a latching mechanism configured to mount the lower arm cuff to the lower cuff mount or the forward cuff mount upon pressing of the lower arm cuff against the lower cuff mount or the forward cuff mount, the latching mechanism resisting dismounting of the lower arm cuff from the lower cuff mount or the forward cuff mount unless the latching mechanism is manually manipulated by pressing on a member of the latching mechanism.

20. The apparatus of claim 15 wherein each cuff of the first one and the second one of the arm support elements comprises:
- a sleeve configured to receive a portion of the arm of the person;
- a band extended about the sleeve, the band having an adjustable effective circumferential length to permit constriction of the band and the sleeve about the portion of the arm of the person; and
- a slider receiving a portion of the band, the slider having a nub.

* * * * *